United States Patent [19]

Hanes

[11] Patent Number: 4,633,021
[45] Date of Patent: Dec. 30, 1986

[54] OLEFIN HYDROFORMYLATION

[75] Inventor: Ronnie M. Hanes, Milford, Ohio

[73] Assignee: National Distillers and Chemical Corporation, New York, N.Y.

[21] Appl. No.: 802,871

[22] Filed: Nov. 29, 1985

[51] Int. Cl.$^4$ ............................................. C07C 45/50
[52] U.S. Cl. ..................................... 568/454; 568/455
[58] Field of Search ........................ 568/454, 451, 455

[56] References Cited

U.S. PATENT DOCUMENTS

| Re. 31,812 | 1/1985 | Kuntz | 568/454 |
| 4,248,802 | 2/1981 | Kuntz | 568/454 |
| 4,510,332 | 4/1985 | Matsumoto et al. | 568/454 |

FOREIGN PATENT DOCUMENTS

| 2627354 | 12/1976 | Fed. Rep. of Germany | 568/454 |
| 2478078 | 9/1981 | France | 568/454 |
| 80/01689 | 8/1980 | PCT Int'l Appl. | 568/454 |

Primary Examiner—Werren B. Lone
Attorney, Agent, or Firm—Kenneth D. Tremain

[57] ABSTRACT

The hydroformylation of olefins to produce aldehydes is disclosed employing an ionic metal complex catalyst where the ionic charge is on either the metal or on a ligand in a polar solvent followed by extracting the aldehyde by means of a hydrocarbon solvent to minimize any deleterious effect on the catalyst which can occur when the aldehyde is separated by other means such as distillation.

29 Claims, No Drawings

OLEFIN HYDROFORMYLATION

DESCRIPTION

1. Technical Field

The present invention generally relates to the production of aldehydes from olefins and, more specifically, to the production of aldehydes by hydroformylation of an olefin, by reacting an olefin with hydrogen and carbon monoxide in the presence of a catalyst.

2. Prior Art

A number of different aldehydes have found a wide range of applications, including use as plasticizers, insecticides, solvents, flavors, spices, perfumes, tanning agents, and chemical intermediates. A variety of methods for their preparation are currently known in the art. Because of the economic importance of these compounds, new methods of preparation which may reduce the cost of production are constantly being sought. Among the commonly used methods for the production of aldehydes is the hydroformylation of an olefin by reaction with hydrogen and carbon monoxide, typically in the presence of a metal catalyst. The aldehydes so produced generally correspond to the compounds obtained by the addition of a carbonyl or carbinol group to an olefinically unsaturated carbon atom in the starting material with simultaneous saturation of the olefinic bond. Although widely employed, the hydroformylation method has certain disadvantages. For example, there is a tendency to generate a relatively high percentage of undesirable iso- or branched isomers of the product, resulting in a low selectivity. Although this drawback may be overcome to a large extent by using a ruthenium catalyst (U.S. Pat. No. 4,306,084), the use of the typical soluble metal catalyst presents a different problem. The recovery and regeneration of dissolved metal catalysts require additional procedures involving special equipment and handling. Such procedures contribute significantly to an unwanted increase in complexity and cost of operations. Distillation procedures which are often used in the process of separating product and catalyst may also adversely affect the catalyst activity. For example, Suss-Fink et al., Jour. of Molec. Catalysis, 16 (1982) 231–242, disclose that when employing the cluster ion $[HRu_3(CO)_{11}]^-$ as a catalyst in hydroformylation reaction using a polar solvent that product can be separated from the catalyst solution only if vacuum distillation is employed at temperatures below 45° C. if the catalyst is to be recycled. Additionally, small losses in recovering and recycling the catalyst are inevitable, further adding to the cost of production.

SUMMARY OF THE INVENTION

The present invention relates to a process for the hydroformylation of olefins for the preparation of aldehydes by reacting carbon monoxide and hydrogen with an olefin, in the presence of an ionic metal complex catalyst where the ionic charge is on either the metal or on a ligand, under suitable conditions of temperature and pressure, the improvement comprising performing the reaction in a polar solvent and separating product from the catalyst by solvent extraction with a hydrocarbon solvent.

It has now been unexpectedly discovered that, with the use of a polar solvent in the typical hydroformylation reaction mixture, the aforementioned disadvantages may be readily overcome. Employing a polar solvent allows recovery of the product by extraction with a hydrocarbon solvent, leaving the catalyst in the polar solvent to be recycled.

The present invention is of particular interest in the preparation of methoxynonenal.

DETAILED DESCRIPTION OF THE INVENTION

As noted above, the present hydroformylation process is superior to those previously known in that it allows a simpler and more effective recovery of the catalyst along with relative ease of extraction of the aldehyde product. It further yields an aldehyde product of relatively high (90%) linearity. In the present process an olefinic organic compound is hydroformylated, under relatively mild conditions, using an ionic metal complex catalyst where the ionic charge is on either the metal or on a ligand, such as $KHRu_3(CO)_{11}$, in the presence of a polar solvent. The use of a polar solvent greatly facilitates extraction of the aldehyde product, by permitting the use of a hydrocarbon solvent for the product extraction. Thus, a separation of product and catalyst is achieved without the necessity for resorting to a potentially damaging distillation process for product recovery. Distillation not only could lead to catalyst decomposition after hydroformylation but also dimerization of the unsaturated aldehyde (e.g. of the methoxynonenal) by an aldol condensation reaction. The method of separation thus also facilitates the process of catalyst recycling.

In the present invention, olefins refer to any olefinic compound. Among the suitable olefins for the present process are 8-methoxy-1,6-octadiene; 8-methoxy-1, 5-octadiene; 8-methoxy-1,4-octadiene; 1,3-butadiene; 2-methyl-1-butene; 2-methyl-1,3-butadiene; 2,3-dimethyl-1, 3-butadiene; 3-methyl-1-pentene; alpha olefins such as propylene; butylene; pentene; hexene and the like, as well as their higher homologues, which may also be otherwise substituted. Generally speaking, any organic compound containing a carbon-to-carbon double bond is contemplated as being within the scope of this invention especially those containing terminal unsaturation. The present invention is of particular interest for use in preparing 9-methoxy-7-nonenal from the starting compound 8-methoxy-1,6-octadiene.

It is preferred to employ a ruthenium catalyst in the present hydroformylation reaction, specifically, an ionic ruthenium carbonyl catalyst. Although these systems do not have exceptionally high activity, they are favored because of their high selectivity for the production of linear aldehydes. Compounds with the highest aldehyde selectivity and highest ratio of linear to branched isomers are those having a potassium counter-cation, although other cations, such as $Na^+$, $Li^+$, $Bu_4P^+$ (where Bu is butyl), $Et_4N^+$ (where Et is ethyl) or benzyl trimethyl ammonium $Bz(meth)_3N^+$ (where meth is methyl) are also effective. Superior catalytic activity is correlated with the presence of the anion $[HM_3(CO)_{11}]^-$; where $M_3$ comprises $Ru_3$; $Ru_2Co$; $Ru_2Fe$; $Rh_2Co$ or $Rh_2Fe$; $Ru_3$ being preferred. The most preferred catalyst for the present system is $KHRu_3CO_{11}$. The desired catalysts may be generated in situ by the addition to the reaction mixture of, for example, $KBH_4$ and $Ru_3(CO)_{12}$, or they may be prepared, separated and added to the reaction mixture.

Cluster ion catalysts that are useful comprise a member selected from the group consisting of $KHM_3(CO)_{11}$, NaHM$_3$(CO)$_{11}$, LiHM$_3$(CO)$_{11}$, Bu$_4$PHM$_3$(CO)$_{11}$, Bz(meth)$_3$NHM$_3$(CO)$_{11}$ and Et$_4$NHM$_3$(CO)$_{11}$ where M$_3$ is selected from Ru$_3$, Ru$_2$Co, Ru$_2$Fe, Rh$_2$Co and Rh$_2$Fe, especially where M$_3$ is Ru$_3$.

Some other preferred cluster ion catalysts comprise:
LiHRu$_3$Co$_{11}$
NaHRu$_3$Co$_{11}$
Bz(meth)$_3$NHRu$_3$Co$_{11}$.

Other catalysts that may be employed comprise:

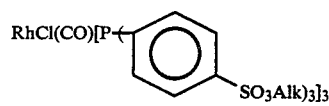

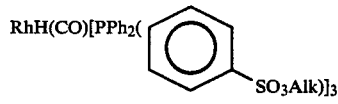

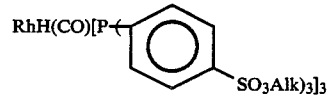

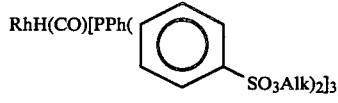

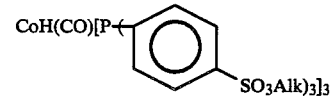

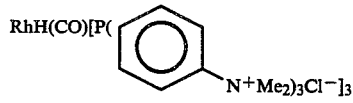

where Alk is Li, K, Na, NH$_4$, Rb or Cs and especially Li, K or Na.

In the present process the olefinic compound is reacted with hydrogen and carbon monoxide under fairly mild conditions of temperature and pressure. Preferably the temperature will be maintained within the range of about 100° to about 300° C., and preferably from about 120° to about 160° C. Most preferred is a temperature of about 130° C. to about 140° C. The pressure is preferably kept within about 400 to about 2000 psig, with the preferred pressure being about 800 psig. Best results are achieved with a H$_2$:CO ratio of about 1:1.

As noted above, the use of a polar solvent in the reaction mixture greatly facilitates product extraction and catalyst recycling. Among the solvents useful in the hydroformylation reaction are N-substituted amides in which each hydrogen of the amido nitrogen is substituted by a hydrocarbyl group, e.g. 1-methylpyrrolidin-2-one; N,N-dimethylacetamide; N,N-diethylacetamide; N,N-dimethylformamide; N-methylpiperidone; 1,5-dimethylpyrrolidin-2-one; 1-benzylpyrrolidin-2-one; N,N-dimethylpropionamide; hexamethylenephosphoric triamide and similar liquid amides and the like; sulfolane; glycols, such as ethylene glycol, propylene glycol, butylene glycol and the like; polyglycols such as polyethylene glycol, polypropylene glycol, polybutylene glycol and mixtures thereof and co-polymers thereof; mono-lower alkyl ethers of alkylene glycols and polyalkylene glycols; e.g. methyl ethers of ethylene glycol, propylene glycol; di-, tri- and tetraethylene glycols; dimethyl sulfoxide (DMSO) and mixtures thereof. Those solvents having a high dielectric constant are the most preferred polar solvents.

Particularly preferred in the process are N,N-dimethylformamide, DMSO or sulfolane.

As previously mentioned, the use of a polar solvent that is a solvent for the catalyst facilitates extraction of the product and recovery and recycling of the catalyst. In the present process, it is possible to extract the aldehyde product from the reaction mixture by using a non-polar hydrocarbon which is a solvent for the aldehyde, such as hexane. The polar and non-polar solvents are selected to form an immiscible pair. Any similar solvent, for example, n-pentane, n-heptane, n-octane, n-nonane, iso-octane, cyclohexane, methylcyclohexane, and the like, and mixtures thereof may be used. Hexane is a preferred organic solvent for extraction. The extraction of the product leaves the catalyst in the polar solvent to be recycled, and thus avoids exposing the catalyst to the fractional distillation process typically used for product-catalyst separation. Multiple extractions can be used since in some cases the aldehyde may also be soluble to some extent in the polar solvent. Co-current or counter-current extraction processes are also utilized according to the invention.

The following examples are illustrative:

EXAMPLE 1

A 300 ml. stirred reactor (without a glass liner) was charged as follows:

| | | |
|---|---|---|
| Ru$_3$(CO)$_{12}$ | 0.198 g | 0.310 mmoles |
| (Benzyltrimethylammonium) hydroxide | 0.2 ml | 0.476 mmoles |
| 8-methoxy-1,6-Octadiene | 96 mls | |
| DMSO | 54 mls | |
| DMF | 5 mls | (Internal Standard) |

After the reactor was charged, it was purged three times with a 1:1 H$_2$:CO mixture and the H$_2$:CO vented. The reactor was then charged with 100 psig of 1:1 H$_2$:CO and heated to 135° C. Once the reaction temperature of 135° C. was obtained, a pressure regulator on the stirred reactor was set to maintain the reaction pressure at 800 psig. The reaction was run for 4 hours and samples taken at 0,1,2,3 and 4 hours and analyzed by glc analysis, the 0 hour sample having been taken before the final 1:1 H$_2$:CO addition. The results obtained are tabulated below:

| Run # | Pressure (psig) CO | Pressure (psig) H$_2$ | Methoxyoctadiene (mmoles) Starting Material | Methoxyoctadiene (mmoles) Isomer 1 (a) | Methoxyoctadiene (mmoles) Isomer 2 (a) | Aldehyde (mmoles) Branched | Aldehyde (mmoles) Linear |
|---|---|---|---|---|---|---|---|
| 0 Hr. | 400 | 400 | 492.4 | 8.2 | 26 | 0.0 | 5.6 |
| 1 Hr. | | | 374.8 | 17.0 | 40.5 | 1.0 | 32.4 |
| 2 Hr. | | | 346.1 | 21.4 | 62.5 | 4.8 | 95.8 |
| 3 Hr. | | | 297.9 | 26.0 | 69.3 | 9.2 | 131.9 |
| 4 Hr. | | | 253.9 | 28.2 | 71.0 | 12.3 | 154.2 |

(a) methoxyoctadiene isomers without terminal unsaturation.

The products obtained were further analyzed to determine aldehyde linearity (percent); aldehyde space time yield in moles/l/hr. and selectivity to linear aldehyde (percent) the results of which are set forth below:

|  | Aldehyde Linearity (%) | Aldehyde Space Time Yield Moles/1/hr. | Selectivity to Linear Aldehyde (%) |
| --- | --- | --- | --- |
| 1 Hr. | 97 | 0.209 | 36 |
| 2 Hr. | 95 | 0.309 | 52 |
| 3 Hr. | 93 | 0.284 | 56 |
| 4 Hr. | 93 | 0.249 | 58 |

The linear aldehyde obtained comprised 9-methoxy-7-nonenal whereas the branched aldehyde comprises 2-methyl-8-methoxy-6-octenal.

EXAMPLE 2

To a 71 cc glass-lined Parr bomb was added 0.0165 g $Ru_3(CO)_{12}$, 0.0027 g $KBH_4$, 5.7 ml sulfolane and 4.3 ml 8-methoxy-1,6-octadiene. The bomb was purged 4 times with $H_2:CO(1:1)$, filled to 2000 psig and placed in a 135° C. shaker oven for 3 hours. A sample was taken for glc analysis and the 9-methoxy-7-nonenal product solution extracted with 20 ml hexane. 3ml methoxyoctadiene was added to the sulfolane layer and returned to the bomb. The bomb was purged 4 times with $H_2:CO$ (1:1), filled to 2000 psig with $H_2:CO(1:1)$ and placed in a 135° C. shaker oven for 3 hours. This was repeated for a total of 5 reaction cycles. The final sulfolane layer was submitted for Ru analysis, as noted below:
0.0165 g $Ru_3(CO)_{12}$ charged = 7.83 mg Ru metal
Ruthenium analysis of final solution = 6.2 mg = 79% recovery of charged Ru.
The results of this example are set forth in Table I.

TABLE I

| $KHRu_3(CO)_{11}$ RECYCLE[1] | | | | |
| --- | --- | --- | --- | --- |
| Cycle | Conversion (%) | Overall Selectivity to Linear Aldehyde (%)[2] | 100 × Linear Ald./Total Mono Alds. | Isomerization (%) |
| A | 51 | 81 |  | 4 |
| B | 47 | 82 | 93 | 3 |
| C | 46 | 84 | 95 | 3 |
| D | 48 | 76 | 88 | 4 |
| E | 41 | 86 | 97 | 2 |

[1]0.0165 g $Ru_3(CO)_{12}$, 0.0027 g $KBH_4$, 5.7 ml sulfolane, 4.3 ml methoxyoctadiene, 2000 psig, 135° C., 3 hrs. Extract with 20 ml hexane, add 5 ml methoxyoctadiene after each cycle.
[2]Linear aldehyde is 9-methoxy-7-nonenal.

EXAMPLE 3

In a first cycle, a 71 cc glass-lined Parr bomb was charged with 0.017 g $Ru_3(CO)_{12}$, 0.0020 g $KBH_4$, 5.7 ml DMF and 4.3 ml 8-methoxy-1,6-octadiene. The bomb was purged 4 times, filled to 2000 psig with $H_2:CO(1:1)$ and placed in a 135° C. shaker oven for 3 hours. The 9-methoxy-7-nonenal product solution was extracted with 20 ml hexane and the DMF layer returned to the bomb with 5 ml methoxyoctadiene. In a second cycle, the bomb was purged 4 times, filled to 2000 psig with $H_2:CO(1:1)$ and placed in a 135° C. shaker oven. After extraction with 20 ml hexane, the DMF solution was submitted for Ru analysis, as noted below:
0.017 g $Ru_3(CO)_{12}$ charged = 8.0 mg Ru metal
Ruthenium analysis of final solution = 7.2 mg = 90% recovery of charged Ru.
The following conversions were obtained:

| Cycle No. | Conversion % |
| --- | --- |
| 1 | 10 |
| 2 | 34 |

EXAMPLE 4

To a 71 cc glass-lined Pan bomb were added 0.164 g (0.0179 mmoles) $RhH(CO)(PPh_3)_3$, 0.1677 g (0.461 mmoles) $Ph_2P(C_6H_4SO_3Na)$, 6.7 ml dimethylsulfoxide (DMSO) and 3.3 ml (19.4 mmoles) methoxyoctadiene. The $RhH(CO)(PPh_3)_3$ and $Ph_2P(C_6H_4SO_3Na)$ form

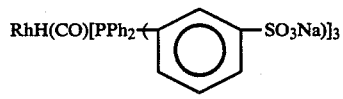

as a catalyst. The bomb was purged 4 times and pressurized to 1000 psig with 2:1 $H_2CO$ and placed in an 80° C. shaker oven, for 2 hours. The bomb was cooled and vented and the product solution was extracted three times with 20 ml aliquots of hexane. To the DMSO layer was added 3.3 ml methoxyoctadiene. This was returned to the bomb and the bomb purged 4 times and pressurized to 1000 psig with 2:1 $H_2:CO$. The bomb was placed in an 80° C. shaker oven for 4 hours. Conversion was 100% in the first cycle and 63% in the second cycle. The yield of 9-methoxy-7-nonenal was 12% in the first cycle and 39% in the second cycle.

Although the invention has been described by reference to some embodiments it is not intended that the novel hydroformylation process be limited thereby but that modifications thereof are intended to be included within the broad scope and spirit of the foregoing disclosure and the following claims:

What is claimed is:

1. In a process for the hydroformylation of olefins for the preparation of aldehydes, by reacting carbon monoxide and hydrogen with an olefin, in the presence of an ionic metal complex catalyst where the ionic charge is on either the metal or on a ligand, at a temperature in the range of between about 80° and about 300° C. and a pressure in the range of between about 400 and about 2000 psig, the improvement comprising performing the reaction in a polar solvent selected from the group consisting of N-substituted amides, glycols, polyglycols, mono lower alkyl ethers of glycols, dimethyl sulfoxide and sulfolane and recovering the aldehyde by extraction with a hydrocarbon solvent.

2. The process of claim 1 wherein the hydrocarbon solvent is hexane.

3. The process of claim 1 which comprises the further steps of recovering and recycling the catalyst.

4. The process of claim 1 wherein the catalyst is an anionic ruthenium carbonyl catalyst.

5. The process of claim 1 wherein the catalyst is selected from the group consisting of $KHM_3(CO)_{11}$, $NaHM_3(CO)_{11}$, $LiHM_3(CO)_{11}$, $Bu_4PHM_3(CO)_{11}$, $Bz(meth)_3NHM_3(CO)_{11}$ and $Et_4NHM_3(CO)_{11}$ where $M_3$ is selected from $Ru_3$, $Ru_2Co$, $Ru_2Fe$, $Rh_2Co$ and $Rh_2Fe$ and

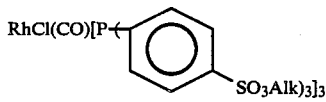
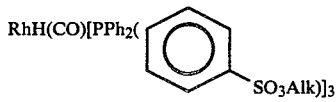
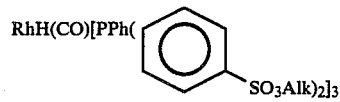
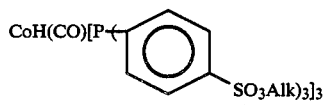
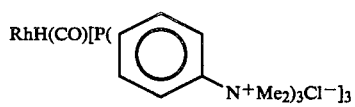

where Alk is Li, K, Na, NH$_3$, Rb or Cs.

6. The process of claim 5 where said M$_3$ is Ru$_3$.

7. The process of claim 5 where said catalyst is LiHRu$_3$(CO)$_{11}$.

8. The process of claim 5 where said catalyst is KHRu$_3$(CO)$_{11}$.

9. The process of claim 5 where said catalyst is NaHRu$_3$(CO)$_{11}$.

10. The process of claim 5 where said catalyst is Bz(meth)$_3$NHRu$_3$(CO)$_{11}$.

11. The process of claim 5 where said catalyst is

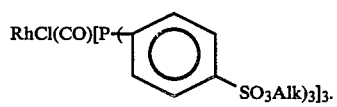

12. The process of claim 5 where said catalyst is

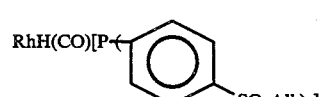

13. The process of claim 5 where in said catalyst is

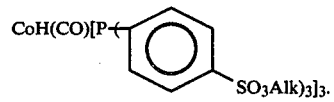

14. The process of claim 1 wherein said solvent is selected from the group consisting of N,N-dimethylformamide, dimethyl sulfoxide and sulfone.

15. The process of claim 1 wherein the temperature is within the range of about 100° C. to about 300° C.

16. The process of claim 15 wherein the temperature is about 130° C. to about 140° C.

17. The process of claim 1 wherein the pressure is within the range of about 800 psig to about 1000 psig.

18. The process of claim 17 wherein the pressure is about 800 psig.

19. A process for the production of 9-methoxy-7-nonenal which comprises hydroformylation of 8-methoxy-1,6-octadiene by reaction with carbon monoxide at a temperature in the range of between about 80° C. and about 300° C. and a pressure in the range of between about 400 and about 2000 psig, in the presence of a cluster ion catalyst in a polar solvent selected from the group consisting of N-substituted amides, glycols, polyglycols, mono lower alkyl ethers of glycols, dimethyl sulfoxide and sulfolane.

20. The process of claim 19 wherein the catalyst is KHRu$_3$(CO)$_{11}$.

21. The process of claim 20 wherein the temperature is between about 100° C. to about 300° C.

22. The process of claim 21 wherein the temperature is about 130° C. to about 140° C.

23. The process of claim 19 wherein the pressure is about 800 to about 1000 psig.

24. The process of claim 23 wherein the pressure is about 800 psig.

25. The process of claim 20 whrein said polar solvent is selected from the group consisting of N,N-dimethylformamide, dimethyl sulfoxide and sulfolane.

26. The process of claim 19 which comprises the further step of extracting the 9-methoxy-7-nonenal with a hydrocarbon solvent.

27. The process of claim 26 wherein the hydrocarbon solvent is hexane.

28. The process of claim 26 which comprises the further step of recovering and recycling the catalyst.

29. The process of claim 19 wherein the catalyst is

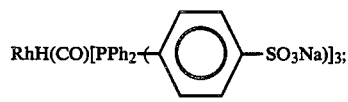

said pressure is about 1000 psig and said temperature is about 80° C.